(12) United States Patent
Fix et al.

(10) Patent No.: US 8,242,599 B2
(45) Date of Patent: Aug. 14, 2012

(54) ELECTRONIC COMPONENT WITH DIFFUSION BARRIER LAYER

(75) Inventors: Richard Fix, Gerlingen (DE); Oliver Wolst, Nuertingen (DE); Alexander Martin, Ludwigsburg (DE)

(73) Assignee: Robert Bosch GmbH, Stuttgart (DE)

( * ) Notice: Subject to any disclaimer, the term of this patent is extended or adjusted under 35 U.S.C. 154(b) by 276 days.

(21) Appl. No.: 12/448,295

(22) PCT Filed: Jan. 9, 2008

(86) PCT No.: PCT/EP2008/050199
§ 371 (c)(1),
(2), (4) Date: Jun. 15, 2009

(87) PCT Pub. No.: WO2008/090023
PCT Pub. Date: Jul. 31, 2008

(65) Prior Publication Data
US 2010/0072621 A1    Mar. 25, 2010

(30) Foreign Application Priority Data

Jan. 24, 2007 (DE) .......................... 10 2007 003 541

(51) Int. Cl.
*H01L 23/532* (2006.01)

(52) U.S. Cl. ........... 257/751; 257/E23.157; 257/E29.16; 257/E29.161; 257/E29.149; 257/E29.253; 257/407; 257/761; 257/750

(58) Field of Classification Search ............... 257/751, 257/E23.157, 407, 761, E29.16, E29.161, 257/750, E29.149, E29.253
See application file for complete search history.

(56) References Cited

U.S. PATENT DOCUMENTS

| 4,437,969 A | 3/1984 | Covington et al. |
| 4,700,462 A * | 10/1987 | Beaubien et al. .............. 438/574 |
| 6,376,888 B1 | 4/2002 | Tsunashima et al. |
| 8,001,828 B2 * | 8/2011 | Hunter et al. ................. 73/31.06 |
| 2003/0129795 A1 * | 7/2003 | Chau et al. ..................... 438/200 |
| 2003/0143825 A1 | 7/2003 | Matsuo et al. |
| 2004/0016984 A1 * | 1/2004 | Lee et al. ....................... 257/473 |
| 2005/0151255 A1 * | 7/2005 | Ando et al. .................... 257/750 |
| 2006/0249847 A1 * | 11/2006 | Eriksen et al. ................. 257/751 |
| 2008/0070401 A1 * | 3/2008 | Park .............................. 438/619 |
| 2009/0113992 A1 * | 5/2009 | Hunter et al. ................. 73/31.06 |
| 2009/0214779 A1 * | 8/2009 | Sarigiannis et al. ........ 427/248.1 |
| 2009/0218643 A1 * | 9/2009 | Kaminaga et al. ............ 257/417 |
| 2009/0224230 A1 * | 9/2009 | Pesetski et al. ................. 257/24 |
| 2010/0059819 A1 * | 3/2010 | Snyder ........................... 257/343 |

* cited by examiner

*Primary Examiner* — A O Williams
(74) *Attorney, Agent, or Firm* — Kenyon & Kenyon LLP

(57) ABSTRACT

An electronic component is described that includes a metallic layer on a substrate that is made of a semiconductor material and a diffusion barrier layer that is made of a material that has a small diffusion coefficient for the metal of the metallic layer which is formed between the metallic layer and the substrate.

19 Claims, 1 Drawing Sheet

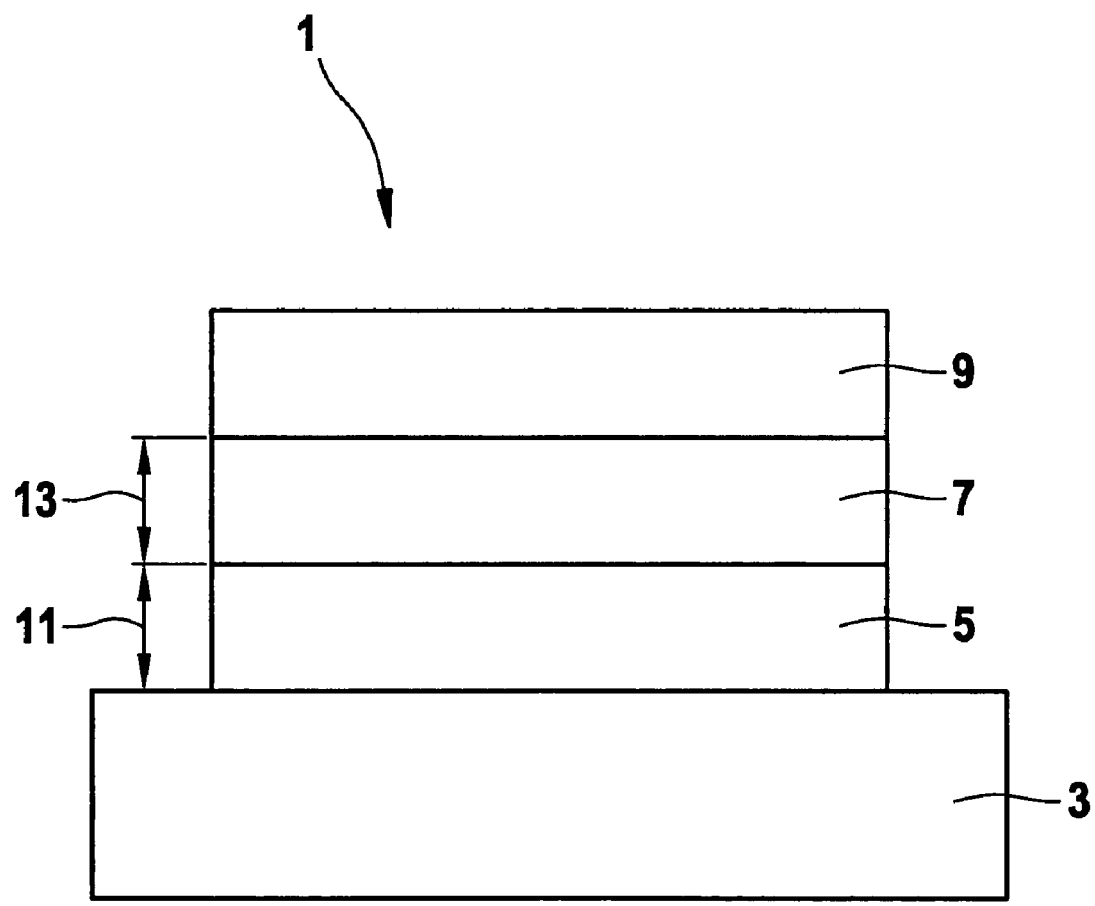

ELECTRONIC COMPONENT WITH DIFFUSION BARRIER LAYER

BACKGROUND OF THE INVENTION

1. Field of the Invention

The present invention relates to an electronic component with a diffusion barrier layer, e.g., a semiconductor transistor.

2. Description of Related Art

A semiconductor transistor is an electronic component having a metallic layer on a substrate made of a semiconductor material. In this instance, the metallic layer is an electrode of the semiconductor transistor, for example.

Platinum or palladium is used as a metal for the metallic layer, for example. In general, it is deposited either directly onto the surface of the semiconductor material or onto electric insulation layers on the semiconductor material. Gallium nitride is a common semiconductor material, for example. However, if the electronic component is used at temperatures above 350° C., the properties of the electronic component may deteriorate irreversibly. For example, this occurs when metal of the metallic layer diffuses or migrates into the electric insulation layer or into the semiconductor material. In the case of transistors, the metal diffusion or migration may cause the channel impedances to change, but also may cause the gate leakage currents to increase drastically. It has also been shown that semiconductor transistors having high gate leakage currents degrade considerably faster than electronic components having low leakage currents. This suggests that electro-migration stimulates a penetration of the platinum of the metallic layer into the semiconductor.

High-performance and high-frequency field-effect transistors, and blue, white, and green LEDs used in opto-electronics are examples of electronic components that use gallium nitride as a semiconductor material. Due to the large band gap of 3.4 eV and the thermal crystal stability of gallium nitride, components based on it are suitable, in principle, for operating temperatures up to approximately 700° C.

A chemically sensitive field-effect transistor is known from U.S. Pat. No. 4,437,969, for example. In this case, the electrodes are formed in a layer construction. The field-effect transistor is operated in liquid media at moderate temperatures. In order to prevent ions from the liquid medium from diffusing into the semiconductor substrate, an ion diffusion barrier is formed between the substrate and the metallic layer. However, this ion diffusion barrier does not prevent metal of the metallic layer from being able to diffuse into the semiconductor substrate at high temperatures.

BRIEF SUMMARY OF THE INVENTION

In an electronic component designed in accordance with the present invention, having a metallic layer on a substrate made of semiconductor material, a diffusion barrier layer is formed between the metallic layer and the substrate, or the metallic layer and an insulation layer, and it is made of a material that has a small diffusion coefficient for the metal of the metallic layer. The diffusion barrier layer reduces the diffusion of metal into the semiconductor material or into the insulation layer. The electronic component is not made unusable by metal diffusing into the semiconductor material, and the insulating property of an electric insulation layer is not impaired by diffused metal.

In the sense of the present invention, "small diffusion coefficient" means that when the electronic component is used, no loss of function due to migration of the metal arises over the lifetime of the electronic component. For many uses, it is necessary for the metal concentration to remain under a critical threshold, $c_{max}$ (e.g., 0.1 atom %), at a given operating temperature over entire lifetime $t_L$, in the section to be protected by the diffusion barrier layer, i.e., the insulation layer or the semiconductor material. According to Fick's law, the following requirement for diffusion coefficient D and barrier layer thickness d may be met as a function of required lifetime $t_L$:

$$\mathrm{erf}\left(\frac{d}{2\sqrt{D \cdot t_L}}\right) > 1 - 2c_{max},$$

erf( ) standing for the Gaussian error integral.

For the example $c_{max}$=0.1 atom %, the following ratio results for layer thickness, diffusion coefficient, and lifetime:

$$\frac{d}{\sqrt{D \cdot t_L}} > 4.38$$

For example, if you assume additionally a lifetime $t_L$, =1000 h and a layer thickness d=10 nm, the following results for diffusion coefficient D of the metal in the diffusion barrier layer:

$$D < 1.5 \cdot 10^{-20} \, \mathrm{cm}^2/\mathrm{s}$$

So that no metal diffuses into the electric insulation layer or the semiconductor material of the substrate, which would render the electronic component unusable, the diffusion barrier layer is preferably pore-free or has only closed pores in the sense that the layer is not pervaded by traversing channels.

So that the operability of the electronic component is not impaired by the diffusion barrier layer, the diffusion barrier layer is preferably made of an electrically conductive material. For example, a silicide, titanium silicon nitride, or wolfram silicon nitride are suitable materials for the diffusion barrier layer. The silicide is preferably tantalum silicide, wolfram silicide, or platinum silicide.

However, alternatively it is also possible for the diffusion barrier layer to be made of a material that is electrically insulating. If the material of the diffusion barrier layer is electrically insulating, it is not necessary to provide an additional electrically insulating layer in order to ensure the functionality of the electronic component and to produce transistors that have low leakage currents even at high temperatures. The semiconductor material of the substrate is preferably gallium nitride. Gallium nitride is a III-V compound semiconductor that is used for high-performance and high-frequency field-effect transistors, for example. Furthermore, gallium nitride is used in opto-electronics, in particular for blue, white, and green LEDs. The advantage of gallium nitride is that due to the large band gap of 3.4 eV and the thermal crystal stability, semiconductor components based on gallium nitride are suitable, in principle, for operating temperatures of up to approximately 700° C.

The material of the metallic layer is preferably a metal of the ninth, tenth, or eleventh group of the periodic system of elements or a mixture of at least two of these metals. It is particularly preferable for the material of the metallic layer to be selected out of platinum, palladium, iridium, gold, silver, rhodium, or a mixture of at least two of these metals. In particular, when the electronic component is used in sensor-system applications, e.g., in the form of a gas-sensitive field-effect transistor, it is particularly advantageous from the electro-chemical point of view to use platinum or palladium as the material for the metallic layer. In sensor-system applications, the metallic layer forms the gate electrode of a field-effect transistor, in particular.

In an example embodiment, an electric insulation layer is also included between the substrate made of the semiconductor material and the metallic layer in order to ensure the functionality of the electronic component. In this context, on the one hand it is possible for the electric insulation layer to be formed between the substrate made of the semiconductor material and the diffusion barrier layer, or for the electrically insulating layer to be formed between the diffusion barrier layer and the metallic layer. Furthermore, it is also possible for a diffusion barrier layer to be located above and below the electric insulation layer. An additional electric insulation layer is advantageous in particular if the diffusion barrier layer is made of an electrically conductive material.

In one example embodiment of the invention, a protective layer is formed above the diffusion layer in order to protect the diffusion barrier layer from oxidation or to prevent materials or oxidation products from leaking out into the diffusion barrier layer. This protective layer may be electrically insulating or conductive. If the protective layer is electrically insulating, it may also function as an electric insulation layer, for example.

The use of the protective layer is preferred in particular when silicides or silicide nitrides are used for the diffusion layer, since their stability and function as a diffusion barrier layer may be impaired by oxidation. For a diffusion barrier layer of silicide or silicide nitride, WSi or WSiN, for example, $Si_3N_4$ is a suitable material for the protective layer, for example. The protective layer is used in particular for use in a corrosive environment and/or at high temperatures.

The preferred material for the electric insulation layer is $Si_3N_4$, for example. If the material of the electric insulation layer is $Si_3N_4$, the diffusion barrier layer may be used as an etch stop layer during the production of the electronic component. Without an etch stop layer, a back etching of the passivation in the section of the gate electrode would also automatically etch away the insulation. A porous metallic layer, as is necessary for gas sensors, for example, could not fulfill this function, however.

An additional advantage of the diffusion barrier layer is also that it may be used as an adhesive agent for the metallic layer on the substrate made of semiconductor material. In particular, platinum and palladium, which are the metals preferably used for gas sensors, already delaminate on a substrate made of gallium nitride starting at a layer thickness of 20 nm. However, if the diffusion barrier layer is used as an adhesive agent, the metallic layer remains adhered to the diffusion barrier layer and does not delaminate.

When the electronic component is used as a gas sensor, it is advantageous if the topmost layer of the diffusion barrier layer has suitable chemical properties relative to the gas surroundings. In particular, this means that the layer provides adsorption spaces for the measuring gas or dissociation or reaction products of the measuring gas, which cause charge separation or dipole formation at the boundary layer. Thus, nitride or oxidic or interface-oxide-forming layers have proven advantageous for $NH_3$, HC, $H_2$ CO and $NO_x$, for example. At the same time, however, it is necessary for this layer to be chemically stable relative to the surroundings. This is fulfilled in particular for the materials already mentioned above for the diffusion barrier layer.

BRIEF DESCRIPTION OF THE DRAWING

FIG. 1 shows by way of example a layer construction of a gate electrode of a semiconductor transistor.

DETAILED DESCRIPTION OF THE INVENTION

An electronic component 1 designed according to the present invention includes a substrate 3, which is made of a semiconductor material. The preferred semiconductor material is gallium nitride. However, in addition to gallium nitride, aluminum nitride, gallium aluminum nitride, and silicon carbide are also suitable as semiconductor material. As described above, gallium nitride is a III-V compound semiconductor that is used for high-performance and high-frequency field-effect transistors, for example. Furthermore, gallium nitride is used in opto-electronics, in particular for blue, white, and green LEDs. Electronic components having a substrate made of gallium nitride are suitable in principle for operating temperatures of up to 700° C. Thus, such components may also be used in high-temperature applications, e.g., for the gas sensor system in exhaust gas flows of motor vehicles.

First, an electric insulation layer 5 is deposited on substrate 3 made of the semiconductor material. Electric insulation layer 5 is preferably made of the same material as the passivation of the chip. For example, $Si_3N_4$ is suitable as the material for electric insulation layer 5. The thickness of electric insulation layer 5 is preferably in the range of 1 to 100 nm.

In general, the material of electric insulation layer 5 is deposited on substrate 3 made of semiconductor material. Thus, for example, an in-situ depositing of $Si_3N_4$ is possible directly after the growth of the semiconductor surface of gallium nitride. Alternatively, however, it is also possible for electric insulation layer 5 to be a CVD (chemical vapor deposition) $Si_3N_4$ layer deposited in an ex-situ manner.

In electronic components having a gate electrode, the gate diode is insulated by electric insulation layer 5, in order to minimize gate leakage currents and thus electro-migration, to stabilize the electric operation, and to ensure a simple signal evaluation. Furthermore, if electric insulation layer 5, as shown in FIG. 1, was deposited directly onto substrate 3, it is possible for it to be used as an adhesive agent for a diffusion barrier having a low interface state density.

A diffusion barrier layer 7 is deposited on electric insulation layer 5. Diffusion barrier layer 7 preferably has a thickness in the range of 1 to 300 nm. The material of diffusion barrier layer 7 is preferably selected such that it has a small diffusion coefficient for the metal of a metallic layer 9 that is deposited on diffusion barrier layer 7. To this end, diffusion barrier layer 7 is preferably essentially pore-free or has only closed pores.

When electronic component 1 is a semiconductor transistor, it is preferred that diffusion barrier layer 7 is made of an electrically conductive material. Through the use of an electrically conductive material for diffusion barrier layer 7, the distance between semiconductor material 3 of the substrate and the source of an electric field is minimized. By this means, the transconductance of the semiconductor transistor is improved. When diffusion barrier layer 7 is produced from an electrically conductive material, the distance between the source of the electric field and the semiconductor material of the substrate only corresponds to thickness 1 of electric insulation layer 5. However, when an electrically insulating material is used for diffusion barrier layer 7, layer thickness 13 of diffusion barrier layer 7 is added to the distance between the source of the electric field and the semiconductor material of substrate 3 and thus reduces the transconductance of the semiconductor transistor. This is because when an insulating material is used for diffusion barrier layer 7, the source of the electric field is only metallic layer 9.

Alternatively, it is also possible to do without an additional electric insulation layer 5 if diffusion barrier layer 7 is made of an electrically insulating material. However, since in general diffusion barrier layer 7 must have a significantly greater layer thickness 13 than an electric insulation layer 5, it is preferable to combine an electrically conductive, thick diffusion barrier layer 7 and a thin electric insulation layer 5, in order to improve the transconductance of electronic component 1 designed as a semiconductor transistor.

The greater layer thickness 13 of diffusion barrier layer 7 relative to thickness 1 of electric insulation layer 5 is necessary in order to achieve a sufficient blocking effect opposite diffusing metal from metallic layer 9 and in this manner to prevent metal from metallic layer 9 from diffusing into the semiconductor material of substrate 3.

An additional advantage of electric insulation layer 5 and additional diffusion barrier layer 7 is that many materials cause open chemical bonds, so-called "dangling bonds," to form when directly deposited onto the semiconductor surface, in particular when the semiconductor material is gallium nitride. Fixed interfacial charges, which impair the transistor properties, result from this. At very high interfacial state densities, it may even be impossible to control the transistor. If a material that may be deposited with very low interfacial state densities is selected for electric insulation layer 5, then improved properties may be achieved, in comparison with the direct depositing of diffusion barrier layer 7 on substrate 3. When gallium nitride is used as a semiconductor material, $Si_3N_4$, for example, has very low interfacial state densities. However, since $Si_3N_4$ is not suitable as a diffusion barrier, an additional diffusion barrier layer 7 is necessary.

The preferred materials for diffusion barrier layer 7 include titanium nitride, an alloy of titanium and wolfram, wolfram, or gold, for example. Furthermore, silicides or nitrides are also suitable, e.g., tantalum silicide, wolfram silicide, molybdenum silicide or platinum silicide, titanium silicon nitride or wolfram silicon nitride, or boron nitride. Tantalum silicide or wolfram silicide are particularly preferred as material for diffusion barrier layer 7.

In general, metallic layer 9 is connected to an electric conductor for operating electronic component 1. Any metal is suitable as a material for the metallic layer. However, the preferred metals are metals of the ninth, tenth, or eleventh group of the periodic system of elements. Platinum, palladium, iridium, gold, silver, rhodium, or a mixture of at least two of these metals is particularly preferable. When electronic component 1 is used as a gas sensor, metallic layer 9 is preferably made of platinum or palladium.

The thickness of metallic layer 9 is preferably in the range of 1 to 100 nm.

When electronic component 1 is used as a gas sensor, the metallic layer is preferably porous. When metallic layer 9 is porous, diffusion barrier layer 7 acts as an additional etch stop layer during the production of electronic component 1. To wit, in general, a passivation is initially deposited on the semiconductor material of substrate 3. To produce the electronic component, this is etched back. Without an etching stop layer, the etching back of the passivation would cause electric insulation layer 5 to be etched away automatically as well. If porous metallic layer 9 were then deposited directly onto electric insulation layer 5, it would not be possible to use it as an etch stop layer, and electric insulation layer 5 would also be etched away. However, diffusion barrier layer 7 prevents electric insulation layer 5 from being etched away even in the event of a porous metallic layer 9.

In addition to the design show here, in which electric insulation layer 5 is deposited on substrate 3 first, then diffusion barrier layer 7, and finally metallic layer 9, it is also possible to deposit diffusion barrier layer 7 on substrate 3 first, and then to deposit subsequently electric insulation layer 5. Furthermore, it is also possible for an additional diffusion barrier layer to be provided. This may be situated between substrate 3 and electric insulation layer 5, for example.

Also, an additional protective layer may be deposited above diffusion barrier layer 7, which prevents materials or oxidation products from leaking out into diffusion barrier layer 7, or prevents an oxidation of diffusion barrier layer 7. Normally, the additional protective layer is situated between diffusion barrier layer 7 and metallic layer 9. In one specific embodiment, when diffusion barrier layer 7 is situated directly on substrate 3, and electric insulation layer 5 is deposited on diffusion barrier layer 7, electric insulation layer 5 is used as an additional protective layer. Alternatively, the additional protective layer may also be included between diffusion barrier layer 7 and electric insulation layer 5.

When an electric insulation layer 5 is not necessary, it is also possible for the additional protective layer to be deposited on diffusion barrier layer 7 instead of on electric insulation layer 5.

What is claimed is:

1. An electronic component, comprising:
    a substrate made of a semiconductor material;
    a metallic layer positioned on the substrate;
    a diffusion barrier layer made of a material having a small diffusion coefficient for the metal of the metallic layer, wherein the diffusion barrier layer is formed between the metallic layer and the substrate; and
    wherein the small diffusion coefficient provides that, when the electronic component is used, there is no substantial loss of function due to migration of the metal.

2. An electronic component, comprising:
    a substrate made of a semiconductor material;
    a metallic layer positioned on the substrate; and
    a diffusion barrier layer made of a material having a small diffusion coefficient for the metal of the metallic layer, wherein the diffusion barrier layer is formed between the metallic layer and the substrate;
    wherein the diffusion barrier layer is substantially pore-free.

3. The electronic component as recited in claim 2, wherein the diffusion barrier layer is made of a material that is electrically conductive.

4. The electronic component as recited in claim 3, wherein the material of the diffusion barrier layer includes one of a silicide, titanium silicon nitride, or wolfram silicon nitride.

5. The electronic component as recited in claim 4, wherein the silicide is one of tantalum silicide or wolfram silicide.

6. The electronic component as recited in claim 3, wherein the semiconductor material of the substrate is gallium nitride.

7. The electronic component as recited in claim 3, wherein the material of the metallic layer includes a metal of at least one of the ninth, tenth, and eleventh group of the periodic table of elements.

8. The electronic component as recited in claim 3, wherein the material of the metallic layer includes at least one of platinum, palladium, iridium, gold, silver, rhodium.

9. The electronic component as recited in claim 3, further comprising:
    an electric insulation layer included between the substrate and the metallic layer.

10. The electronic component as recited in claim 9, wherein the electric insulation layer is made of $Si_3N_4$.

11. The electronic component as recited in claim 3, wherein the metallic layer is a gate electrode.

12. The electronic component as recited in claim 9, wherein an additional protective layer is deposited onto the diffusion barrier layer.

13. The electronic component as recited in claim 12, wherein the material for the additional protective layer is $Si_3N_4$.

14. A gas sensor, which is an electronic component, comprising:
   a substrate made of a semiconductor material;
   a metallic layer positioned on the substrate;
   a diffusion barrier layer made of a material having a small diffusion coefficient for the metal of the metallic layer, wherein the diffusion barrier layer is formed between the metallic layer and the substrate; and
   wherein the small diffusion coefficient provides that, when the electronic component is used, there is no substantial loss of function due to migration of the metal.

15. A method for making an electronic component for use as a gas sensor, the method comprising:
   forming a substrate made of a semiconductor material;
   positioning a metallic layer on the substrate;
   forming a diffusion barrier layer between the metallic layer and the substrate, wherein the diffusion barrier layer is made of a material having a small diffusion coefficient for the metal of the metallic layer; and
   wherein the small diffusion coefficient provides that, when the electronic component is used, there is no substantial loss of function due to migration of the metal.

16. The method as recited in claim 15, wherein the electronic component is configured as a gas-sensitive field-effect transistor.

17. A method for making an electronic component for use as a gas sensor, the method comprising:
   forming a substrate made of a semiconductor material;
   positioning a metallic layer on the substrate; and
   forming a diffusion barrier layer between the metallic layer and the substrate, wherein the diffusion barrier layer is made of a material having a small diffusion coefficient for the metal of the metallic layer;
   wherein the electronic component is configured as a gas-sensitive field-effect transistor, and wherein the metallic layer is made of platinum.

18. The method as recited in claim 16, wherein the metallic layer is made of palladium.

19. The method as recited in claim 16, wherein the diffusion barrier layer has suitable chemical properties relative to the gas surroundings.

* * * * *